US011077261B2

(12) United States Patent
Liu

(10) Patent No.: US 11,077,261 B2
(45) Date of Patent: Aug. 3, 2021

(54) ELECTRONIC CIGARETTE

(71) Applicant: Tuanfang Liu, Shenzhen (CN)

(72) Inventor: Tuanfang Liu, Shenzhen (CN)

( * ) Notice: Subject to any disclaimer, the term of this patent is extended or adjusted under 35 U.S.C. 154(b) by 420 days.

(21) Appl. No.: 16/265,964

(22) Filed: Feb. 1, 2019

(65) Prior Publication Data

US 2019/0289911 A1 Sep. 26, 2019

(30) Foreign Application Priority Data

Mar. 24, 2018 (CN) .......................... 201820404144.7
Nov. 6, 2018 (CN) .......................... 201811310497.1

(51) Int. Cl.
*A61M 11/04* (2006.01)
*A24F 7/00* (2006.01)
*A61M 15/06* (2006.01)
*H01M 50/209* (2021.01)
*A24F 40/485* (2020.01)
*A24F 15/015* (2020.01)
*A24F 40/10* (2020.01)

(52) U.S. Cl.
CPC ............ *A61M 11/042* (2014.02); *A24F 7/00* (2013.01); *A24F 40/485* (2020.01); *A61M 15/06* (2013.01); *H01M 50/209* (2021.01); *A24F 15/015* (2020.01); *A24F 40/10* (2020.01); *A61M 2205/8206* (2013.01); *H01M 2220/30* (2013.01)

(58) Field of Classification Search
CPC .............. A61M 11/042; A61M 15/06; A61M 2205/8206; A24F 40/285; A24F 40/10

USPC .......................................................... 131/329
See application file for complete search history.

(56) References Cited

U.S. PATENT DOCUMENTS

| 9,924,742 | B2 * | 3/2018 | Liu | ........................ A24F 40/40 |
|---|---|---|---|---|
| 10,045,567 | B2 * | 8/2018 | Monsees | ............... A61M 15/06 |
| 10,058,130 | B2 * | 8/2018 | Monsees | .................. A24F 7/00 |
| 10,201,188 | B2 * | 2/2019 | Lin | .......................... F16B 7/20 |
| 10,279,934 | B2 * | 5/2019 | Christensen | ............ B65B 3/003 |
| 2014/0174458 | A1 * | 6/2014 | Katz | ......................... A24F 1/00 |
| | | | | 131/200 |
| 2014/0190477 | A1 * | 7/2014 | Qiu | ......................... A24F 40/44 |
| | | | | 128/202.21 |
| 2014/0196734 | A1 * | 7/2014 | Liu | ........................ A24F 40/40 |
| | | | | 131/329 |
| 2014/0261493 | A1 * | 9/2014 | Smith | ..................... A24F 40/40 |
| | | | | 131/328 |

(Continued)

*Primary Examiner* — Alexander Gilman
(74) *Attorney, Agent, or Firm* — Matthias Scholl P.C.; Matthias Scholl

(57) ABSTRACT

An electronic cigarette, including an atomizing assembly and a battery assembly. The atomizing assembly is disposed on the battery assembly. The atomizing assembly includes a mouthpiece cover, a mouthpiece, a rubber ring, a regulating ring, a first fixed ring adapted to fixing the regulating ring, a silica ring, a connector, an upper seal ring, an atomization core, a first pressure sheet, a positive terminal, a positive silicone, a connection tube, an upper cover, a first seal ring sealing the upper cover, an e-liquid conservator, a lower seal ring, a second fixed ring, a second pressure sheet, a second seal ring, a filling pipe, a first spring, a filling funnel, a third seal ring sealing the filling funnel, and a fourth seal ring. The rubber ring and the silica ring are disposed on two ends of the connector, respectively. The regulating ring is disposed on the connector.

4 Claims, 5 Drawing Sheets

(56) References Cited

U.S. PATENT DOCUMENTS

| | | | | |
|---|---|---|---|---|
| 2015/0013701 A1* | 1/2015 | Liu | ................. | A24F 40/40 |
| | | | | 131/329 |
| 2015/0027467 A1* | 1/2015 | Liu | ................. | A61M 15/06 |
| | | | | 131/329 |
| 2015/0059784 A1* | 3/2015 | Liu | ................. | A24F 40/40 |
| | | | | 131/329 |
| 2015/0201674 A1* | 7/2015 | Dooly | ................. | A24F 40/40 |
| | | | | 53/432 |
| 2015/0223522 A1* | 8/2015 | Ampolini | ................. | H01C 3/16 |
| | | | | 131/328 |
| 2016/0095354 A1* | 4/2016 | Wu | ................. | A24F 40/485 |
| | | | | 131/329 |
| 2016/0262450 A1* | 9/2016 | Liu | ................. | H01M 50/116 |
| 2016/0338405 A1* | 11/2016 | Liu | ................. | A24F 40/40 |
| 2016/0353798 A1* | 12/2016 | Liu | ................. | A24F 40/40 |
| 2016/0366936 A1* | 12/2016 | Liu | ................. | H05B 1/0244 |
| 2017/0071252 A1* | 3/2017 | Liu | ................. | A24F 40/70 |
| 2017/0162979 A1* | 6/2017 | Liu | ................. | A24F 40/40 |
| 2017/0172207 A1* | 6/2017 | Liu | ................. | A24F 40/40 |
| 2017/0208868 A1* | 7/2017 | Li | ................. | B65D 81/264 |
| 2018/0013104 A1* | 1/2018 | Qiu | ................. | A24F 40/40 |
| 2018/0103684 A1* | 4/2018 | Liu | ................. | A24F 7/02 |
| 2019/0289911 A1* | 9/2019 | Liu | ................. | A61M 15/06 |
| 2019/0357595 A1* | 11/2019 | Liu | ................. | F16J 15/324 |

* cited by examiner

# ELECTRONIC CIGARETTE

CROSS-REFERENCE TO RELATED APPLICATIONS

Pursuant to 35 U.S.C. § 119 and the Paris Convention Treaty, this application claims foreign priority to Chinese Patent Application No. 201820404144.7 filed Mar. 24, 2018, and to Chinese Patent Application No. 201811310497.1 filed Nov. 6, 2018. The contents of all of the aforementioned applications, including any intervening amendments thereto, are incorporated herein by reference.

BACKGROUND

This disclosure relates to an electronic cigarette.

Electronic cigarettes atomize nicotine-containing e-liquid.

Conventionally, the atomizing assembly fixedly communicates with the battery assembly. This increases the difficulty in replacing the atomization core. In addition, the atomizing core tends to slide out in the process of regulating the volume flow rate of the vapor. This increases the risk of unwanted leakage of the e-liquid.

SUMMARY

The disclosure provides an electronic cigarette.

Provided is an electronic cigarette, comprising an atomizing assembly and a battery assembly. The atomizing assembly is disposed on the battery assembly.

The atomizing assembly comprises a mouthpiece cover, a mouthpiece, a rubber ring, a regulating ring, a first fixed ring adapted to fixing the regulating ring, a silica ring, a connector, an upper seal ring, an atomization core, a first pressure sheet, a positive terminal, a positive silicone, a connection tube, an upper cover, a first seal ring adapted to seal the upper cover, an e-liquid conservator, a lower seal ring, a second fixed ring, a second pressure sheet, a second seal ring, a filling pipe, a first spring, a filling funnel, a third seal ring adapted to seal the filling funnel, and a fourth seal ring.

The rubber ring and the silica ring are disposed on two ends of the connector, respectively; the regulating ring is disposed on the connector; the first fixed ring is disposed on the regulating ring; the connector is connected to the atomization core, and the upper seal ring is disposed in the connector and adapts to seal one end of the connection tube; the atomization core is disposed in the connection tube; the mouthpiece and the mouthpiece cover are disposed on the connection tube.

The positive terminal is disposed in the positive silicone; the positive silicone is disposed in the connection tube; the lower seal ring is disposed in the connection tube; the second fixed ring is fixed on the connection tube; the connection tube is disposed in the e-liquid conservator; the first seal ring is disposed on the upper cover; the upper cover is disposed on the e-liquid conservator; and the first pressure sheet is disposed on the connection tube.

The fourth seal ring, the second pressure sheet, the third seal ring and the first spring are sequentially disposed on the filling funnel; the filling funnel is inserted in the filling pipe; the second seal ring is disposed on the filling pipe; the filling pipe is disposed in the e-liquid conservator. The battery assembly comprises first screws, a steel sheet, a button support, a button, a middle frame, reverse springs, elastic fasteners, output thimbles, second springs, a thimble support, fasteners, third fixed rings, a printed circuit board, a cover plate, second screws, a first cushion, a battery cell, a second cushion, a third cushion, and a base frame.

The first cushion, the second cushion, and the third cushion encircle the battery cell; the battery cell is disposed in the base frame; the cover plate is fixed on the base frame via the second screws; the printed circuit board is disposed on the cover plate.

The output thimbles and the second springs are disposed on the thimble support and are fixed via the third fixed rings; the thimble support is fixed on the cover plate; the steel sheet is disposed on the thimble support and fixed via the first screws; and the reverse springs are disposed at two sides of the thimble support; the elastic fasteners are disposed on the reverse springs; the button support is attached to the button, and disposed in the middle frame; the fasteners are disposed at two sides of the middle frame, and the base frame is inserted in the middle frame.

The regulating ring comprises locating slots, and the connector can comprise stop pins corresponding to the locating slots.

The first pressure sheet can comprise polyformaldehyde.

The first cushion, the second cushion and the third cushion can comprise an ethylene-vinyl acetate copolymer.

Advantages of the electronic cigarette according to embodiments of the disclosure are summarized as follows. The atomizing assembly communicates with the battery assembly via the fasteners disposed at two sides of the battery assembly. This simplifies the dismantling of the electronic cigarette and facilitates the replacement of the atomizing assembly. The regulating ring comprises locating slots, and the connector of the atomization core comprises stop pins corresponding to the locating slots, so that in the process of regulating the volume of the vapor, the atomization core will not detach. The opening and closing of the e-liquid injection end is controlled by the filling tunnel, the fourth seal ring and the second pressure sheet, improving the sealing properties of the electronic cigarette.

DETAILED DESCRIPTION

To further illustrate, embodiments detailing an electronic cigarette are described below. It should be noted that the following embodiments are intended to describe and not to limit the disclosure.

Figure 1:
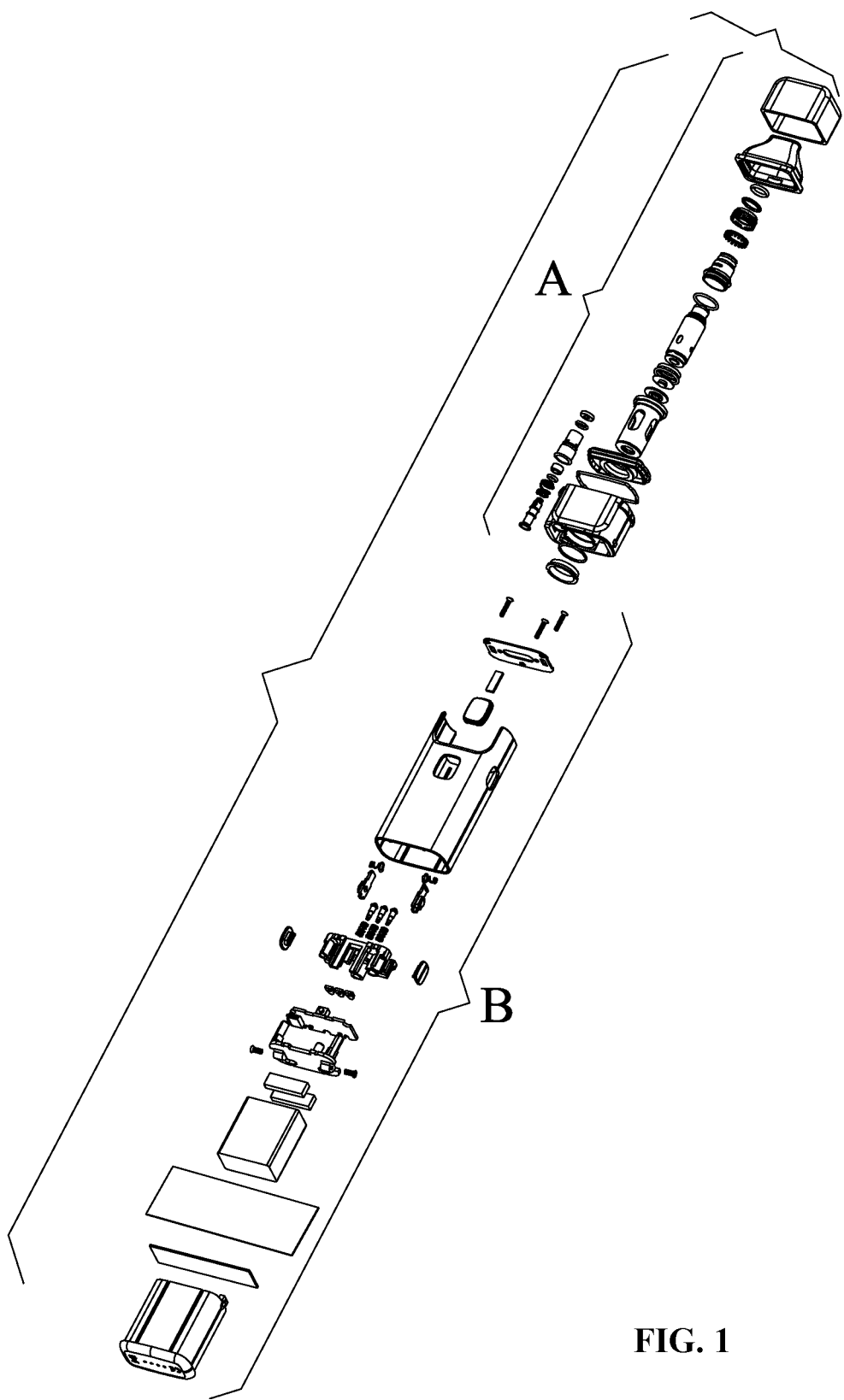
FIG. 1 is an exploded view of an electronic cigarette as described in the disclosure.
Figure 2:
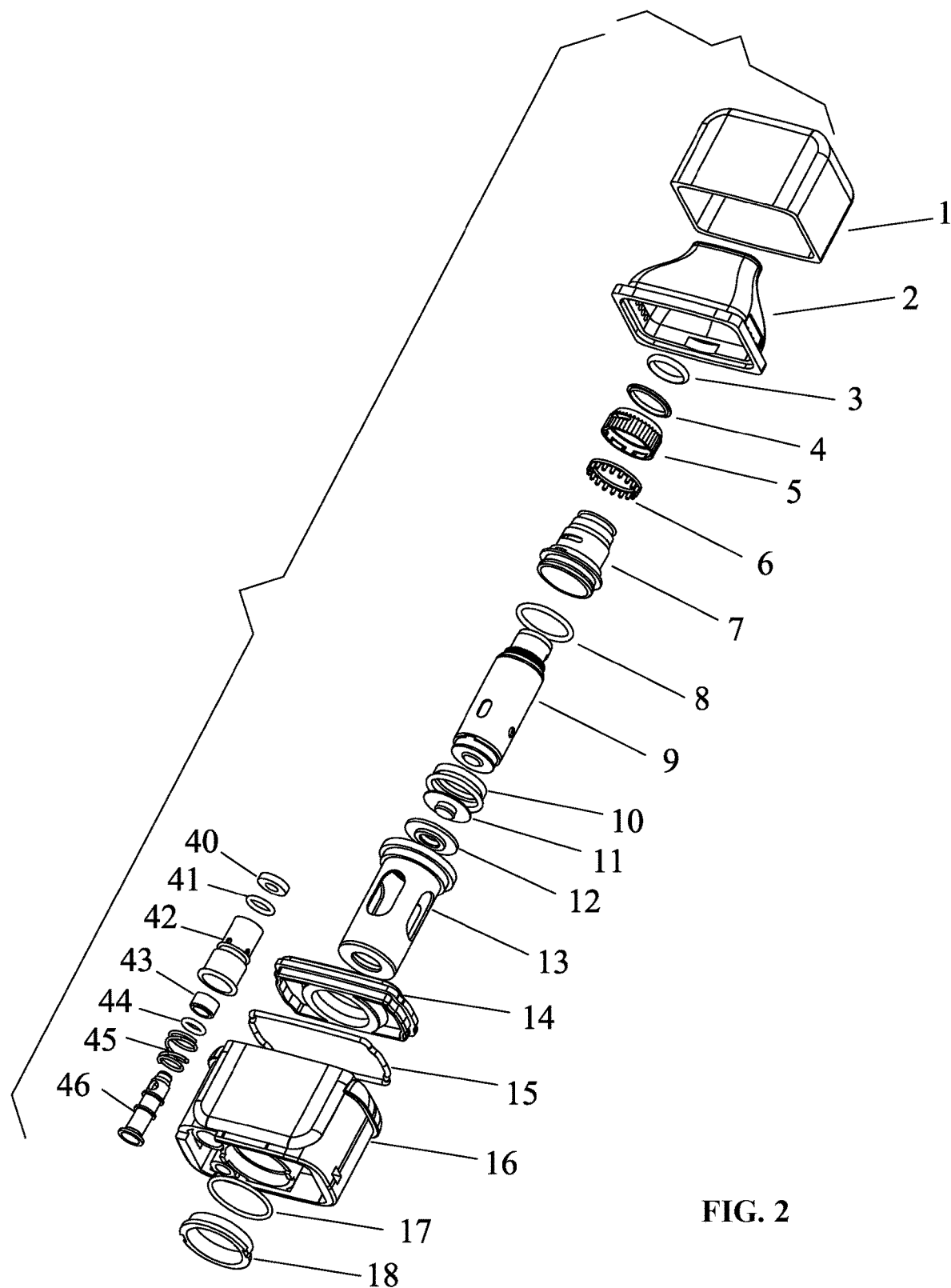
FIG. 2 is an exploded view of an atomizing assembly of an electronic cigarette as described in the disclosure.
Figure 3:
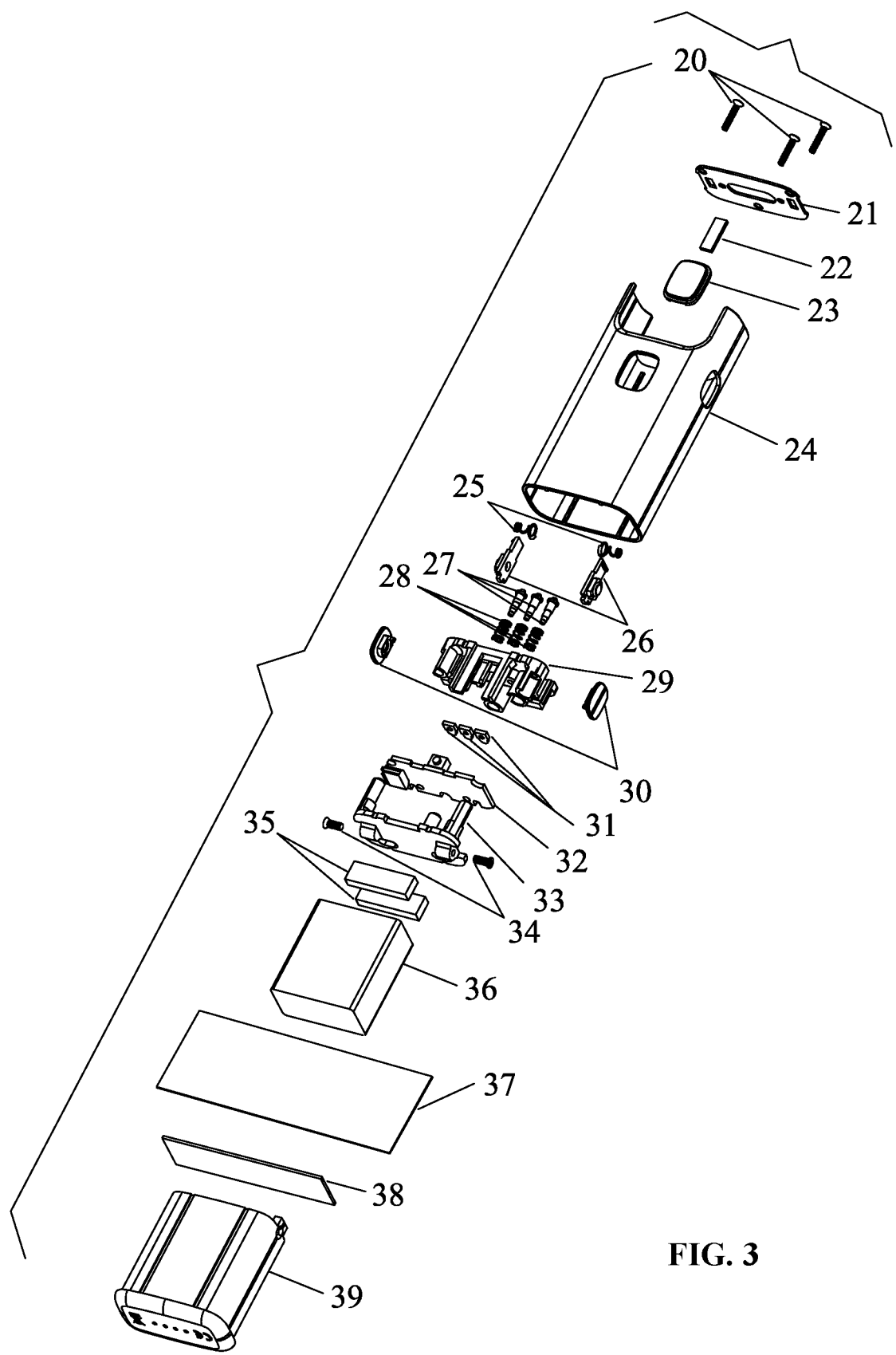
FIG. 3 is an exploded view of a battery assembly of an electronic cigarette as described in the disclosure.
Figure 4:
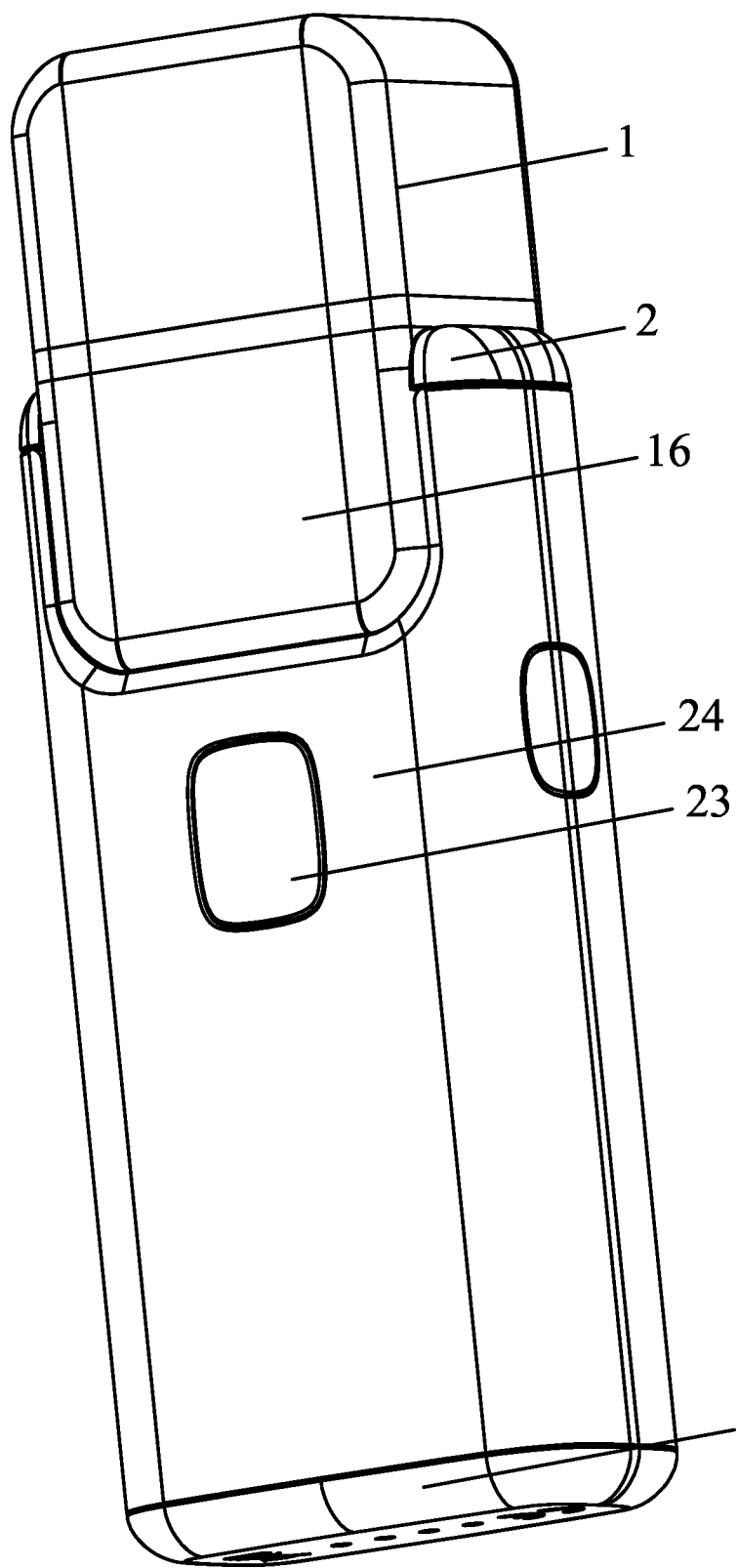
FIG. 4 is a stereogram of an electronic cigarette as described in the disclosure.
Figure 5:
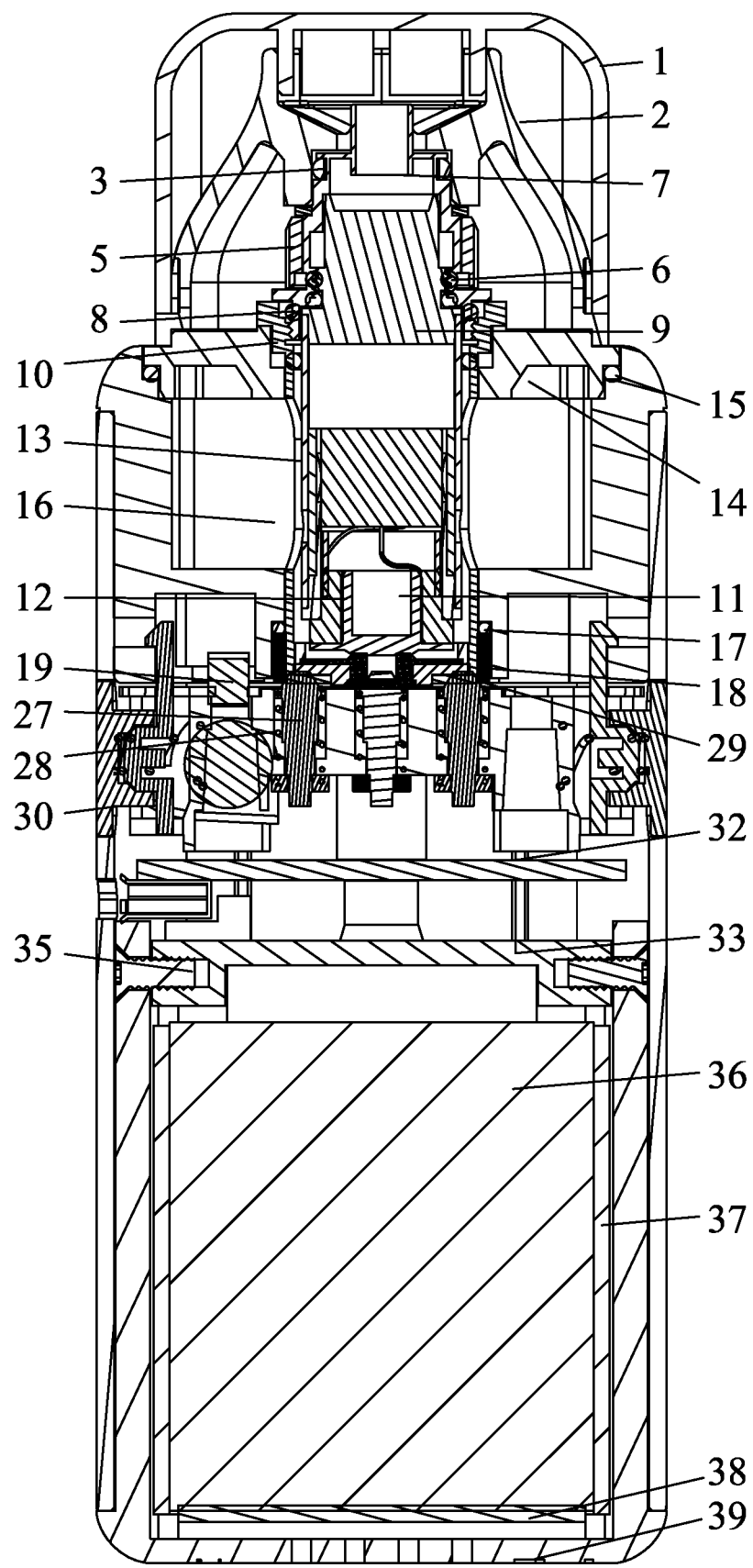
FIG. 5 is a sectional view of an electronic cigarette as described in the disclosure.

As shown in FIGS. 1-5, provided is an electronic cigarette, comprising: an atomizing assembly A; and a battery assembly B. The atomizing assembly A is disposed on the battery assembly B.

The atomizing assembly A comprises a mouthpiece cover 1, a mouthpiece 2, a rubber ring 3, a regulating ring 5, a first fixed ring 4 adapted to fixing the regulating ring, a silica ring 6, a connector 7, an upper seal ring 8, an atomization core 9, a first pressure sheet 10, a positive terminal 11, a positive silicone 12, a connection tube 13, an upper cover 14, a first seal ring 15 adapted to seal the upper cover 14, an e-liquid conservator 16, a lower seal ring 17, a second fixed ring 18, a second pressure sheet 40, a second seal ring 41, a filling pipe 42, a first spring 45, a filling funnel 46, a third seal ring 43 adapted to seal the filling funnel 46, and a fourth seal ring 44.

The rubber ring 3 and the silica ring 6 are disposed on two ends of the connector 7, respectively; the regulating ring 5 is disposed on the connector 7; the first fixed ring 4 is disposed on the regulating ring 5; the connector 7 is connected to the atomization core 9, and the upper seal ring 8 is disposed in the connector 7 and adapts to seal one end of the connection tube; the atomization core 9 is disposed in the connection tube 13; the mouthpiece 2 and the mouthpiece cover 1 are disposed on the connection tube 13.

The positive terminal 11 is disposed in the positive silicone 12; the positive silicone 12 is disposed in the connection tube 13; the lower seal ring 17 is disposed in the connection tube 13; the second fixed ring 18 is fixed on the connection tube 13; the connection tube 13 is disposed in the e-liquid conservator 16; the first seal ring 15 is disposed on the upper cover 14; the upper cover 14 is disposed on the e-liquid conservator 16; and the first pressure sheet 10 is disposed on the connection tube 13.

The fourth seal ring 44, the second pressure sheet 40, the third seal ring 43 and the first spring 45 are sequentially disposed on the filling funnel 46; the filling funnel 46 is inserted in the filling pipe 42; the second seal ring 41 is disposed on the filling pipe 42; the filling pipe 42 is disposed in the e-liquid conservator 16.

Upon filling the e-liquid, press the filling funnel 46, the e-liquid injection end of the filling funnel 46 is exposed out of the filling pipe 42, the e-liquid is injected into the e-liquid conservator 16. Thereafter, the filling funnel 46 returns to the filling pipe 42. The e-liquid injection end is tightly sealed in the filling pipe 42 via the fourth seal ring 44 and the second pressure sheet 40, preventing the leakage of the e-liquid. The regulating ring 5 comprises locating slots, and the connector 7 comprises stop pins corresponding to the locating slots. The regulating ring 5 adapts to regulate the volume of the vapor. To replace the atomization core, press the regulating ring 5 to enable the locating slots to be clamped in the stop pins of the connector 7, and then rotate the regulating ring to screw out the atomization core.

The battery assembly B comprises first screws 20, a steel sheet 21, a button support 22, a button 23, a middle frame 24, reverse springs 25, elastic fasteners 26, output thimbles 27, second springs 28, a thimble support 29, fasteners 30, third fixed rings 31, a printed circuit board 32, a cover plate 33, second screws 34, a first cushion 35, a battery cell 36, a second cushion 37, a third cushion 38, and a base frame 39; the first cushion 35, the second cushion 37 and the third cushion 38 encircles the battery cell 36; the battery cell 36 is disposed in the base frame 39; the cover plate 33 is fixed on the base frame 39 via the second screws 34; the printed circuit board 32 is disposed on the cover plate 33; the output thimbles 27 and the second springs 28 are disposed on the thimble support 29 and are fixed via the third fixed rings 31; the thimble support 29 is fixed on the cover plate 33; the steel sheet 21 is disposed on the thimble support 29 and fixed via the first screws 20; and the reverse springs 25 are disposed at two sides of the thimble support 29; the elastic fasteners 26 are disposed on the reverse springs 25; the button support 22 is attached to the button 23, and disposed in the middle frame 24; the fasteners 30 are disposed at two sides of the middle frame 24, and the base frame 39 is inserted in the middle frame 24.

The atomizing assembly is fixed on the battery assembly via the fasteners 30 disposed at two sides of the middle frame. To dismantle the electronic cigarette, synchronously press the fasteners 30 disposed at two sides of the middle frame, and then the atomizing assembly can be detached from the battery assembly, thus facilitating the replacement of the atomizing assembly.

It will be obvious to those skilled in the art that changes and modifications may be made, and therefore, the aim in the appended claims is to cover all such changes and modifications.

What is claimed is:

1. An electronic cigarette, comprising:
    an atomizing assembly; and
    a battery assembly;
   wherein:
    the atomizing assembly is disposed on the battery assembly;
    the atomizing assembly comprises a mouthpiece cover, a mouthpiece, a rubber ring, a regulating ring, a first fixed ring adapted to fixing the regulating ring, a silica ring, a connector, an upper seal ring, an atomization core, a first pressure sheet, a positive terminal, a positive silicone, a connection tube, an upper cover, a first seal ring adapted to seal the upper cover, an e-liquid conservator, a lower seal ring, a second fixed ring, a second pressure sheet, a second seal ring, a filling pipe, a first spring, a filling funnel, a third seal ring adapted to seal the filling funnel, and a fourth seal ring;
    the rubber ring and the silica ring are disposed on two ends of the connector, respectively; the regulating ring is disposed on the connector; the first fixed ring is disposed on the regulating ring; the connector is connected to the atomization core, and the upper seal ring is disposed in the connector and adapts to seal one end of the connection tube; the atomization core is disposed in the connection tube; the mouthpiece and the mouthpiece cover are disposed on the connection tube;
    the positive terminal is disposed in the positive silicone; the positive silicone is disposed in the connection tube; the lower seal ring is disposed in the connection tube; the second fixed ring is fixed on the connection tube; the connection tube is disposed in the e-liquid conservator; the first seal ring is disposed on the upper cover; the upper cover is disposed on the e-liquid conservator; and the first pressure sheet is disposed on the connection tube;
    the fourth seal ring, the second pressure sheet, the third seal ring and the first spring are sequentially disposed on the filling funnel; the filling funnel is inserted in the filling pipe; the second seal ring is disposed on the filling pipe; the filling pipe is disposed in the e-liquid conservator;
    the battery assembly comprises first screws, a steel sheet, a button support, a button, a middle frame, reverse springs, elastic fasteners, output thimbles, second springs, a thimble support, fasteners, third fixed rings, a printed circuit board, a cover plate, second screws, a first cushion, a battery cell, a second cushion, a third cushion, and a base frame;
    the first cushion, the second cushion and the third cushion encircle the battery cell; the battery cell is disposed in the base frame; the cover plate is fixed on the base frame via the second screws; the printed circuit board is disposed on the cover plate;

the output thimbles and the second springs are disposed on the thimble support and are fixed via the third fixed rings; the thimble support is fixed on the cover plate; the steel sheet is disposed on the thimble support and fixed via the first screws; and the reverse springs are disposed at two sides of the thimble support; the elastic fasteners are disposed on the reverse springs; the button support is attached to the button, and disposed in the middle frame; the fasteners are disposed at two sides of the middle frame, and the base frame is inserted in the middle frame.

2. The electronic cigarette of claim 1, wherein the regulating ring comprises locating slots, and the connector comprises stop pins corresponding to the locating slots.

3. The electronic cigarette of claim 1, wherein the first pressure sheet is a polyformaldehyde pressure sheet.

4. The electronic cigarette of claim 1, wherein the first cushion, the second cushion and the third cushion comprise an ethylene-vinyl acetate copolymer.

\* \* \* \* \*